(12) United States Patent
Miller

(10) Patent No.: US 6,318,998 B1
(45) Date of Patent: Nov. 20, 2001

(54) GLUE-FREE DENTAL ARTICULATOR AND METHOD OF USE

(76) Inventor: Douglas Eugene Miller, 1612 E. Unaka Ave., Johnson City, TN (US) 37601

( * ) Notice: Subject to any disclaimer, the term of this patent is extended or adjusted under 35 U.S.C. 154(b) by 0 days.

(21) Appl. No.: 09/709,207

(22) Filed: Nov. 10, 2000

(51) Int. Cl.7 .................................................. A61C 11/00
(52) U.S. Cl. ............................... 433/64; 433/60; 433/213
(58) Field of Search ................................. 433/60, 63, 64, 433/54, 213, 57

(56) References Cited

U.S. PATENT DOCUMENTS

| | | |
|---|---|---|
| 4,378,929 | 4/1983 | Huffman . |
| 4,382,787 | 5/1983 | Huffman . |
| 4,449,930 | 5/1984 | Huffman . |
| 4,481,162 | 11/1984 | Huffman . |
| 4,494,934 | 1/1985 | Huffman . |
| 4,533,323 | 8/1985 | Huffman . |
| 4,548,581 | 10/1985 | Huffman . |
| 4,734,033 | 3/1988 | Huffman . |
| 4,786,253 | 11/1988 | Morais . |
| 4,797,097 | 1/1989 | Cohn . |
| 4,842,242 | 6/1989 | Huffman . |
| 4,865,544 | 9/1989 | Scruggs . |
| 5,100,317 | 3/1992 | Darnand . |
| 5,360,337 | 11/1994 | Westdyk . |
| 5,425,636 | 6/1995 | Ghim . |
| 5,482,460 | 1/1996 | Farnor, Jr. . |
| 5,605,456 | 2/1997 | Young . |
| 5,957,688 | 9/1999 | Van Valey . |

*Primary Examiner*—Nicholas D. Lucchesi

(57) ABSTRACT

The present invention provides a low-cost, durable dental articulator that does not require the use of toxic or messy glues. The articulator is composed of a pair of bands that encircle and are attached to the plaster upper and lower teeth bases of the model, a pair of spheres that mechanically attach to the bands at any of several positions corresponding to the rear of the mouth on the dental model, and a hinge assembly simulating movement of the jaw and made of two arcs attached to each other at their ends by a hinge mechanism and having clamps at their apexes for attaching to the spheres. The dental model can be adjusted to mimic the occlusion of the patient by adjusting the position at which the spheres are attached to the bands and the position of the spheres in the clamps.

16 Claims, 10 Drawing Sheets

PRIOR ART

90

92

GLUE-FREE DENTAL ARTICULATOR AND METHOD OF USE

FIELD OF THE INVENTION

The present invention relates to low cost, glue-free dental model articulators and methods of making them.

BACKGROUND OF THE INVENTION

A dental articulator is used to connect dental models of upper and lower sets of teeth and to simulate the movement of the patient's jaw. Early articulators were large, cumbersome devices, usually made of metal, and the teeth models were attached to them with plaster. The next generation of articulators were also metal, but they were smaller and easier to manipulate. The models still attached to them with plaster, however, and the process of articulation remained time-consuming and messy. The most common articulators currently used in the field are made entirely of plastic. Models are attached to the articulators with super glue instead of plaster, and they are much easier to handle and work. The current system, however, does offer opportunities for improvement.

The VERTEX articulator system sold by Ceramco of Burlington, N.J., represents the type of articulators currently used in the art. See FIG. 1. The VERTEX system consists of three parts: plastic sockets (1), plastic hinges (2) having mounted plastic balls (3) matching the plastic sockets and rubber base molds (4 and 5). The rubber base mold is customarily in the form of a half mold (4) which allows the modeling of an entire set of upper or lower teeth, or a quarter mold (5), which allows only modeling of one half of a set of upper or lower teeth. Plaster is poured into the rubber base mold (4 or 5), model teeth (not shown) are anchored in the upper surface of the uncured plaster and then the plaster is allowed to set. After curing, the upper teeth hardened base and lower teeth hardened base containing the model teeth are removed from their respective rubber molds. The plastic sockets (1) are then glued to the ends of an upper teeth hardened base and a lower teeth hardened base. The plastic balls (3) on the hinges (2) are then inserted into the sockets (1) and the model teeth in the molds are aligned to match the natural bite (occlusion) of the subject. Once the model teeth are properly aligned, the balls (3) are glued into place in the sockets (1) to fix them in that alignment, while the hinges (2) are left freely moving to represent opening and closing of the mouth.

This system suffers from several drawbacks. The super glue used (cyano acrylate) is hazardous and unpleasant to work with. The entire hinge unit, including the sockets, easily breaks off of the hardened base, and the rubber base molds accumulate bits of hardened plaster over time, particularly in its corners, which mar the surface of the base units made in them and makes removal of the hardened base unit increasingly difficult over time.

Accordingly, it is an object of this invention to provide a low cost, plastic, dental-model articulator which is less likely to break away from the dental model base.

It is a further object of this invention to provide a low-cost, plastic, dental-model articulator which does not require the use of glue to assemble the finished, articulated dental model.

It is yet another object of this invention to provide a method of forming an articulated dental model with fewer mold marks and improved strength in the attachment of the articulating hinge to the upper and lower teeth bases.

It is still another object of this invention to provide a significant improvement in the physical protection of the model base and the model teeth.

SUMMARY OF THE INVENTION

The foregoing objects are achieved by the dental articulator and method of articulating a dental model described below. The dental articulator of the instant invention is constructed of a pair of substantially inflexible bands for encircling the upper and lower dental model bases, a pair of spheres with attached mechanical means for securing them to one of several attachment sites formed on the outer surface of the substantially inflexible bands, and a hinge assembly formed of a pair of elastic arcuate arms joined at their ends by a hinge mechanism and having at their apexes opposing grips for clamping one of the spheres between them. The grips can be spread enough to admit the sphere between them by flexing the arcuate arm, and after the flexion is released, the grips clamp the sphere with sufficient force to prevent relative motion between the sphere and the clamps. By attachment of the sphere to different attachment sites on the substantially inflexible band and rotation between the hinge assembly and the upper and lower dental model bases allowed by adjusting the clamping location on the sphere, an articulation which mimics the bite of the patient can be achieved.

Advantages of the instant articulator include the avoidance of toxic and messy glue, which has previously been necessary to attach an attachment site to the dental model bases and to fix the attachment of the hinges to the attachment site; the ability to readjust the articulation at any time, which was impossible with glue use; a lower incidence of breakage in the articulator; and improved durability, appearance and strength of the dental model bases, the plaster of which is now protected by the band that surrounds it.

The pair of substantially inflexible bands is provided for encircling the upper and lower plaster bases of the dental model. The substantially inflexible bands include a retaining means for extending into the plaster base and securing the substantially inflexible bands to the plaster base. Preferably, this retaining means is a protrusion, such as a rib, on the interior surface of the band, and the plaster base of the dental model is formed by placing the substantially inflexible band on a base mold cap to form a mold, pouring uncured plaster into the mold and allowing it to cure, thereby embedding the protrusion in the plaster. Alternatively, the substantially inflexible band can be placed around an already formed plaster base and any known retaining means can be used to attach them together, such as nails or screws. The band provides a durable cover for the plaster base and a smooth, attractive side for the plaster base, absent the mold marks encountered with prior art articulators. The substantially inflexible bands also provide at least one attachment site for the sphere on their outer surface. Preferably, the attachment site is a molded form which mechanically mates with a molded form on the sphere to firmly attach the sphere to the band. Alternatively, the attachment site could simply be an outer surface on the substantially inflexible band to which the sphere can be attached by mechanical means such as a nail, screw or rivet attached to the sphere. The bands must be substantially inflexible so that they form a good mold for pouring plaster into and so that they form a secure anchor site.

The sphere has an attached mechanical means for securing the sphere to the attachment site on the substantially inflexible band. Preferably, the mechanical means is a molded part which mates with the molded form of the attachment site to provide a secure, glueless attachment. Alternatively, the mechanical means could be a means of attaching to the band by penetrating it, such as a nail, screw or rivet. The surface of the sphere is preferably textured, in order to increase the friction and reduce the chance of relative motion between it and the working clamp.

The hinge assembly is composed of two elastic arcuate arms connected to each other at their ends by a hinge mechanism. At the apex of the convex side of each arcuate arm is a pair of opposing grips which are sized and shaped to clamp the sphere between them. By compressing the two ends of an arcuate arm toward each other, the arc is flexed and the opposing grips will be separated sufficiently to place them around the sphere. Once the flexing of the arc is released, the elastic arc returns to a position in which the opposing grips are forced together to clamp the sphere with sufficient pressure to prevent relative rotation of the sphere between the grips. Preferably, the portions of the grips which contact the sphere are also textured to increase friction and the security of the clamping. If the operator wishes to adjust the angle at which the grips hold the sphere (and therefore the relative angle of the upper or lower dental models), she can simply compress the arcuate arms again, adjust the angle and release the arms to reclamp and resecure the dental model in the new position. Most preferably, the two elastic arcuate arms are identical, each having a ball on one end and a socket on the other, so that any two arcuate arms can be placed ball to socket and socket to ball to form the hinge mechanism that emulates the movement of the human jaw in the dental model.

DEFINITIONS

For the purposes of the present invention, "mechanical means for securing" will mean all non-glue means of mechanically securing one item to another. "Plaster" will mean plaster, gypsum-based stone, die stone, silica-based stone, phosphate investments, or any other modeling substrates used in the dental arts.

DETAILED DESCRIPTION OF PREFERRED EMBODIMENTS

Figure 1:
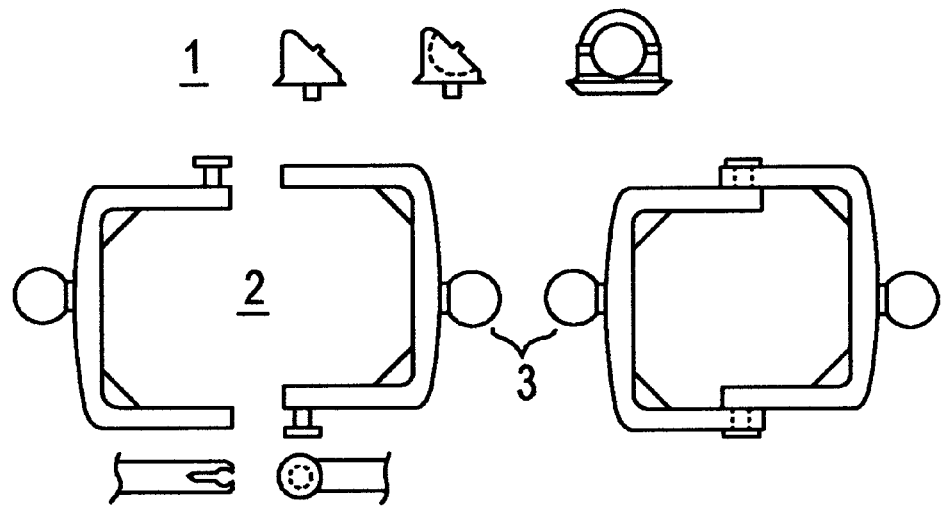
FIG. 1 shows several views of a prior art dental model articulator and a mold in which parts of the model are made.
Figure 1:
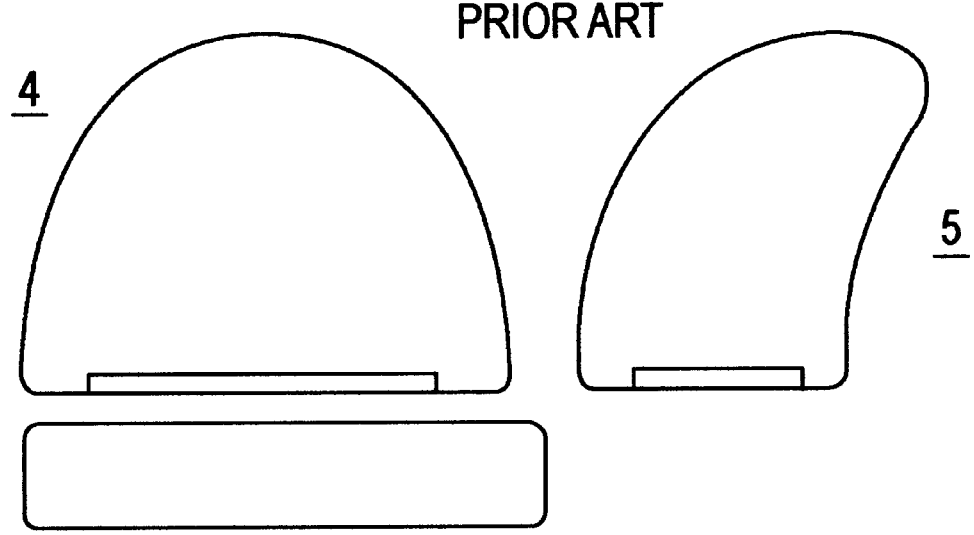
Figure 2:
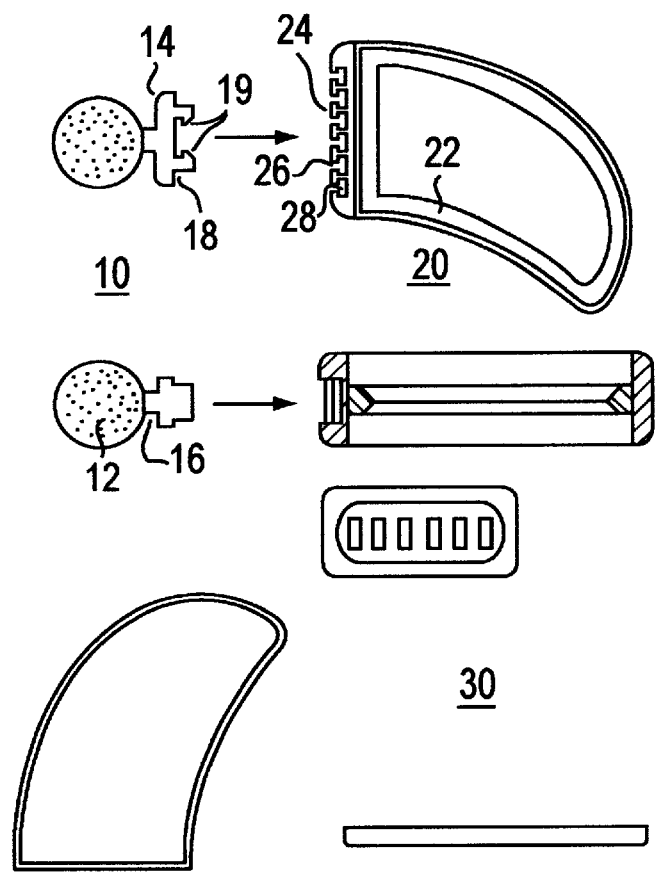
FIG. 2 shows the master ball, base mold band and base mold cap of a first preferred embodiment of the invention.

The master ball (10), base mold band (20) and base mold cap (30) of a first preferred embodiment of the glue-less articulating system are shown in FIG. 2. Dental models of either an entire set of teeth or just one side of the mouth can be made using the half band or quarter band, respectively, of the base mold band and base mold cap.

The base mold band (20) is made from a substantially inflexible material, such as plastic or metal, and is shaped to circumvent the plaster base of the dental model and provide the plaster base with a desired shape. The preferred circumferential shapes of the plaster base in the dental modeling industry are a quarter band for modeling only one side of the mouth, or a half band for modeling of a full set of teeth, although other shapes could easily be made. The height of the base mold band determines the maximum depth of the plaster base of the dental model.

The base mold band (20) preferably has a rib (22) or one or more extensions on an inner surface which, after the wet plaster has been poured into the center of the base mold band, will extend into the plaster. Once the plaster is cured, these embedded retention means will secure the plaster in the base mold band. Alternatively, where the base mold band does not have any integral retention means, nails, spikes or screws can be embedded into the plaster through the base mold band in order to secure the cured plaster. These nails, spikes or screw can be embedded into the plaster before or after curing.

The base mold band (20) also has one or more attachment sites (24) on its outer surface to which the master ball (10) can be attached without the need for glue. Several identical attachments sites can be included in the outer surface in order to allow alternate attachment positions for the master ball and the resulting modeling of different bite patterns between the upper and lower modeled teeth. The attachments sites (24) are found on the outer surface of the base mold band in positions which will correspond to the rear of the modeled mouth, once the dental model has been assembled. In this particular embodiment, the attachment sites (24) are slots in the base mold band. These slots are narrowest at their openings (26) and contain a wider portion (28) in their depths.

The master ball (10) is composed of a sphere (12), preferably with a textured surface, attached to a catch (14) by a neck (16). The catch has two prongs (18) on it with barbed ends (19) which are spaced to match the distance between two of the slots on the base mold band. The barbed ends (19) are sized so that the barbed ends are wider than the opening (26) of the slots of the base mold band, but of lesser or equal width than the wider portion (28) in the depth of the slot. The barbed ends (19) are formed of a resilient material so that they can be forced past the narrow opening (26) of the slot, and the direction of the barb prevents the removal of the prong from the slot, once the barb is anchored in the wider portion (28) in the depth of the anchoring slot.

The base mold cap (30) is made from a flexible material, preferably a synthetic rubber, which does not substantially adhere to the plaster before, during or after the plaster curing process. The base mold cap is sized and shaped to cover a lower opening of the base mold band.

The combination of the base mold band and the base mold cap provide a form into which the plaster can be poured for forming the base of a dental model. The model teeth are anchored in the plaster before it cures. After curing, the base mold cap is peeled away from the bottom of the dental model base. The base mold band remains on the dental model base as an aesthetic and protective covering, as well as providing a secure means for attachment of the articulating hinges without requiring glue.

Figure 3:
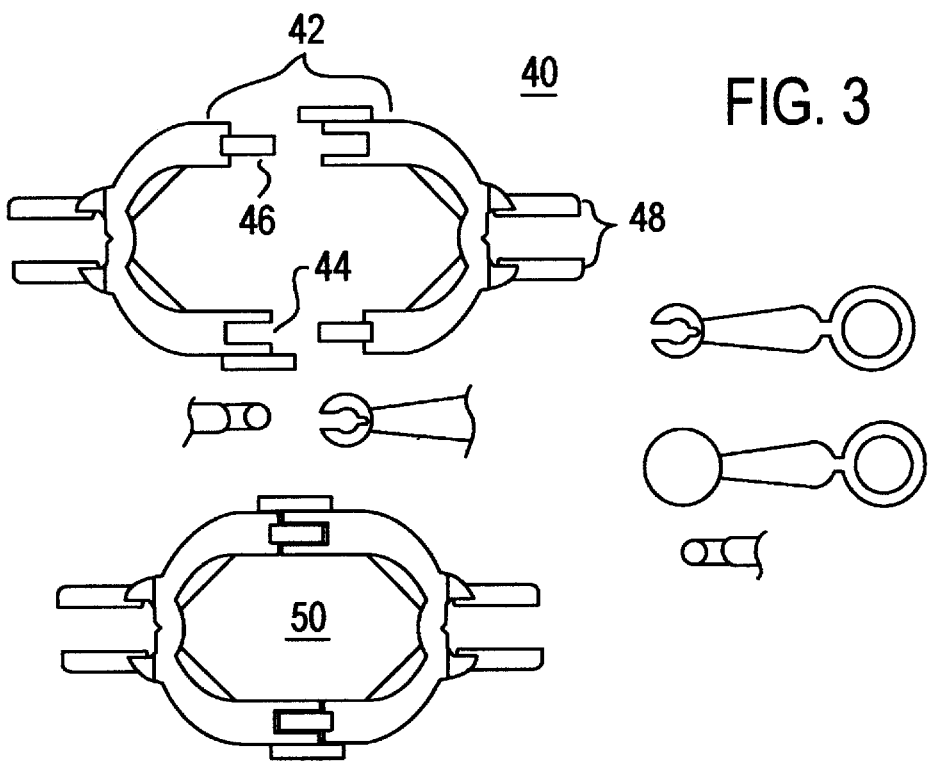
FIG. 3 shows the hinge assembly of the first preferred embodiment of the invention.

The hinge assembly (40) of the first preferred embodiment is shown in FIG. 3. The hinge assembly is formed of two molded plastic arcs (42), which can be fitted together to form a hinge (50). For economy and ease of manufacture, it is preferred for the two arcs to be identical. Each arc has a mating pin (44) and socket (46) at opposite ends of the arch, so that any two arcs can be snapped together to form a hinge (50) by matching up the pin and socket of the first arc to the socket and pin, respectively, of the second arc and snapping the pins into the sockets. The two pin and socket joints formed serve as a hinge that simulates the hinge of the human jaw. Each arc has at its peak a pair of clamp rings (48) facing each other and sized to accept the sphere of the master ball (12).

Figure 4:
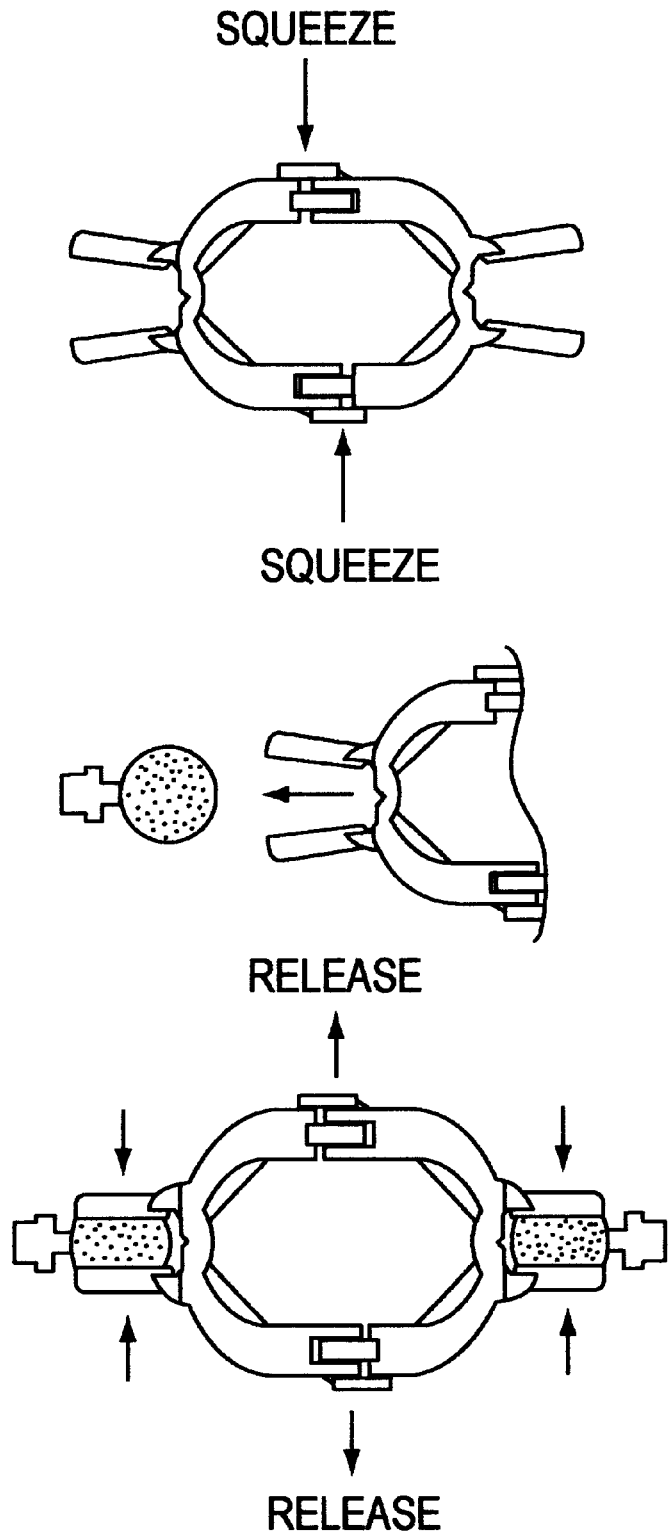
FIG. 4 shows operation of the assembled hinge of the first preferred embodiment of the invention.

The clamp rings of any arc can be spread by squeezing the ends of the arc toward each other. See FIG. 4. Spreading the clamp rings allows the sphere of the master ball to be placed between them. When the squeezing pressure on the ends of the arc is released, the clamp rings engage the surface of the sphere of the master ball and friction prevents or retards relative motion between the surface of the sphere of the master ball and the inner surface of the clamp rings. In order to better secure the master ball in the clamp rings, one or both of the exterior of the sphere or the interior of the cups may be textured. Alternatively, the surface of the sphere of the master ball and the interior of the clamp rings may have mating protuberances and depressions.

Figure 5:
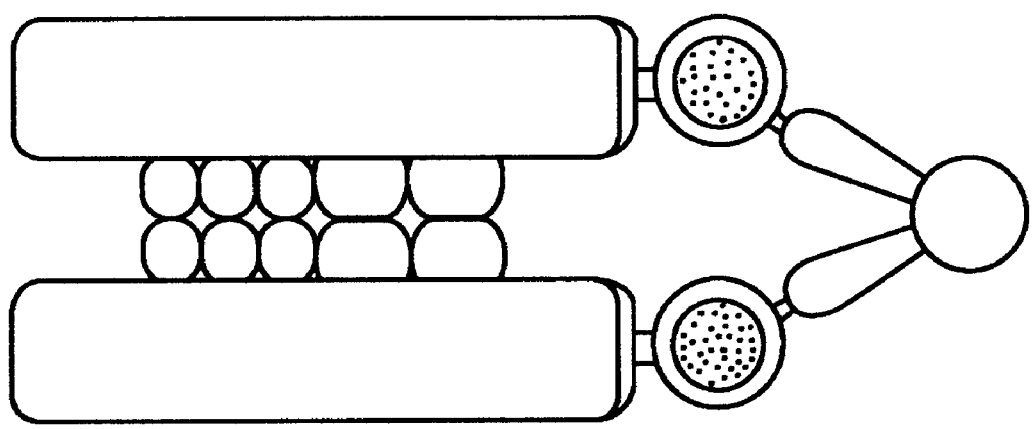
FIG. 5 shows an assembled dental model according to the first preferred embodiment.

A fully assembled dental model according to the first embodiment is shown in FIG. 5.

Figure 6:
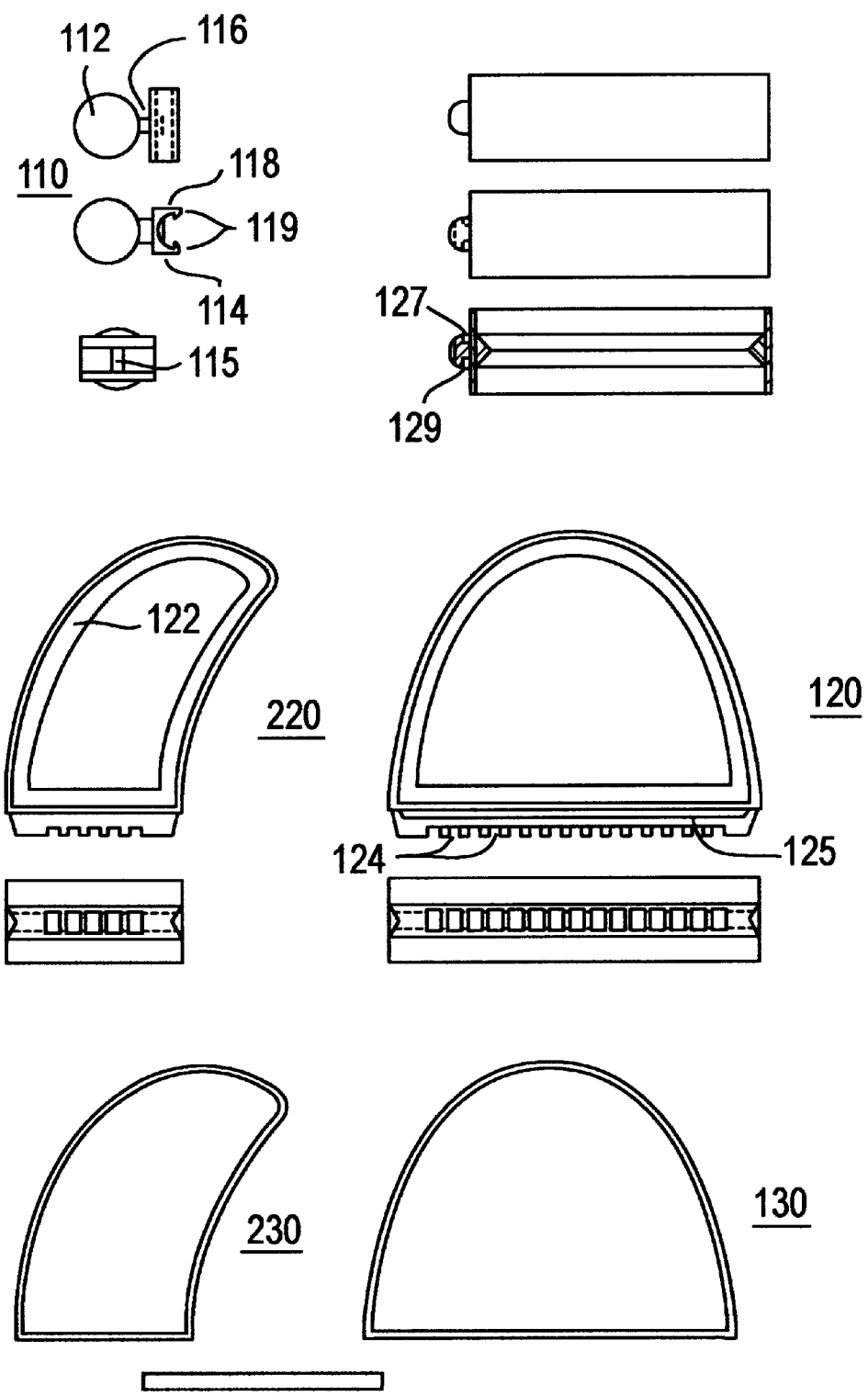
FIG. 6 shows the master ball, base mold band and base mold cap of a second preferred embodiment of the invention.

The master ball (110), base mold band (120 and 220) and base mold cap (130 and 230) of a second preferred embodiment of the glue-less articulating system are shown in FIG. 6. Again, dental models of either an entire set of teeth or just one side of the mouth can be made using the half band (120 and 130) or quarter band (220 and 230), respectively, of the base mold band and base mold cap.

The base mold band (120 or 220) is made from a substantially inflexible material, such as plastic or metal, and is shaped to circumvent the plaster base of the dental model and provide the plaster base with a desired shape. The height of the base mold band determines the maximum depth of the plaster base of the dental model, The base mold band (120 or 220) preferably has a rib (122) or one or more extensions on an inner surface which, after the wet plaster has been poured into the center of the base mold band, will extend into the plaster. Once the plaster is cured, these embedded retention means will secure the plaster in the base mold band.

The base mold band (120 or 220) also has one or more attachment sites (124) on its outer surface to which the master ball (110) can be attached without the need for glue. Several identical attachments sites can be included in the outer surface in order to allow alternate attachment positions for the master ball and the resulting modeling of different bite patterns between the upper and lower modeled teeth. In this particular embodiment, the attachments sites (124) are slots in and transverse to a raised rail (125) on that outer surface of the base mold band which will correspond to the rear of the modeled mouth, once the dental model has been assembled. The raised rail (125) contains upper (127) and lower (129) channels substantially parallel to the raised rail. Each of the upper and lower channels run by all the attachment sites on the raised rail and preferably run substantially the entire length of the raised rail.

The master ball (110) is composed of a sphere (112), preferably with a textured surface, attached to a C-shaped catch (114) by a neck (116). The catch has two prongs (118) on it with barbed ends (119). The prongs (118) are spaced to pass over the raised rail (125) and the barbed ends (119) act to engage the upper (127) and lower (129) channels. The barbed ends (119) are angled and formed of a sufficiently resilient material to allow them to be forced over the raised rail and into the channels, but not to allow removal of the master ball along a transverse direction from the raised rail A tongue (115) transverse to the prongs mates with an attachment site slot (124) to prevent movement of the installed master ball along the raised rail.

The base mold cap (130) is made from a flexible material, preferably a synthetic rubber, which does not substantially adhere to the plaster before, during or after the plaster curing process. The base mold cap is sized and shaped to cover a lower opening of the base mold band.

Figure 7:
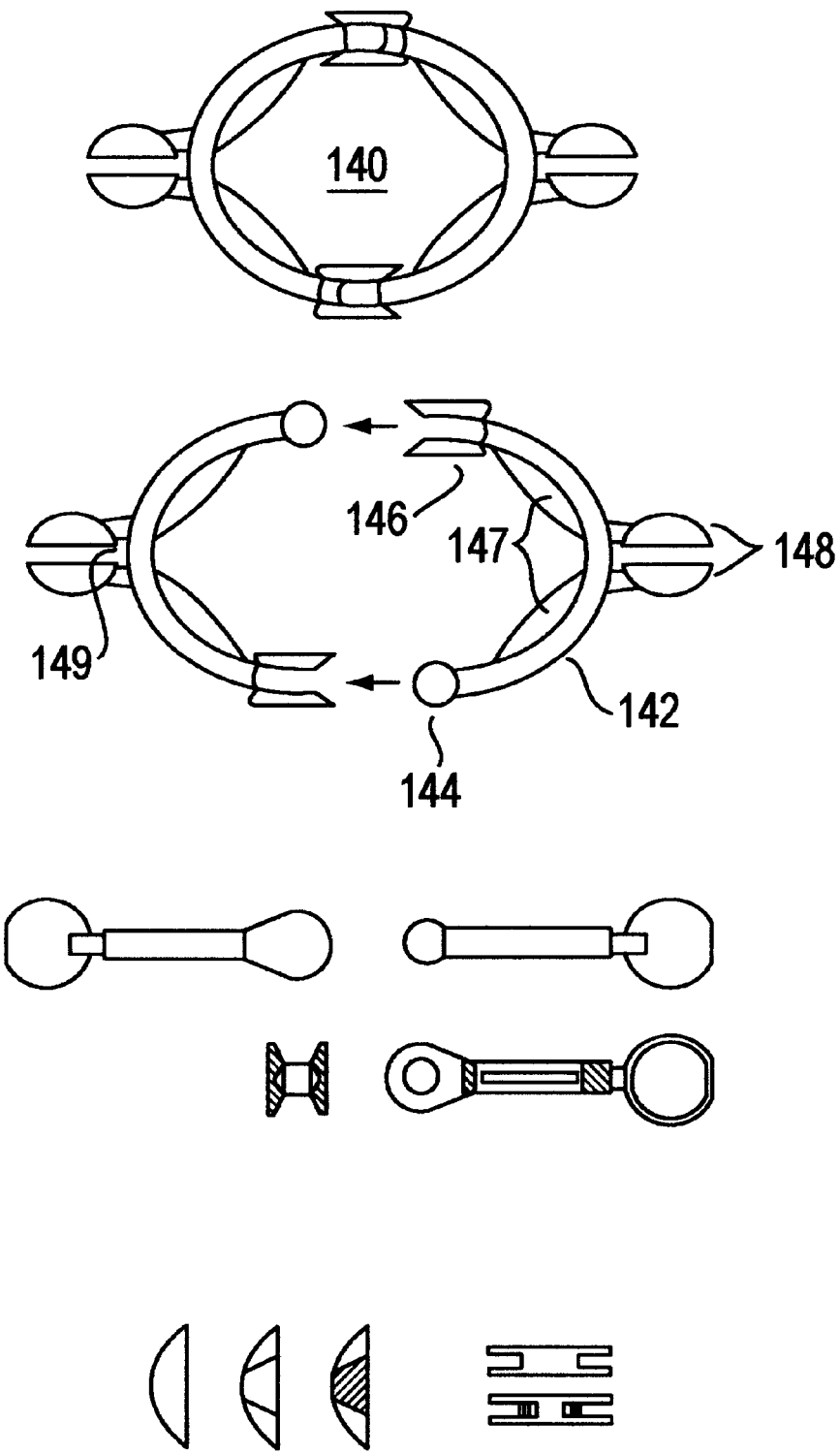
FIG. 7 shows the hinge assembly and wedge lock of the second preferred embodiment of the invention.

The hinge assembly (140) of the second preferred embodiment is shown in FIG. 7. The hinge assembly is formed of two identical molded plastic arcs (142), which can be fitted together to form a hinge. Each arc has a mating ball (144) and socket (146) at opposite ends of the arch, so that any two arcs can be snapped together to form a hinge by matching up the ball and socket of the first arc to the socket and ball, respectively, of the second arc and snapping the balls into the sockets. The two ball and socket joints formed serve as a hinge that simulates the hinge of the human jaw. Each arc has at its peak a pair of cups (148) facing each other and sized to accept the master ball (112). Each arc also has a pair of rib braces (147), which strengthen those sections of the arc that are not desirable to flex, and flex point (149), which is a notch in the arc that focuses the flexing of a compressed arc at the apex of the arc.

Figure 8:
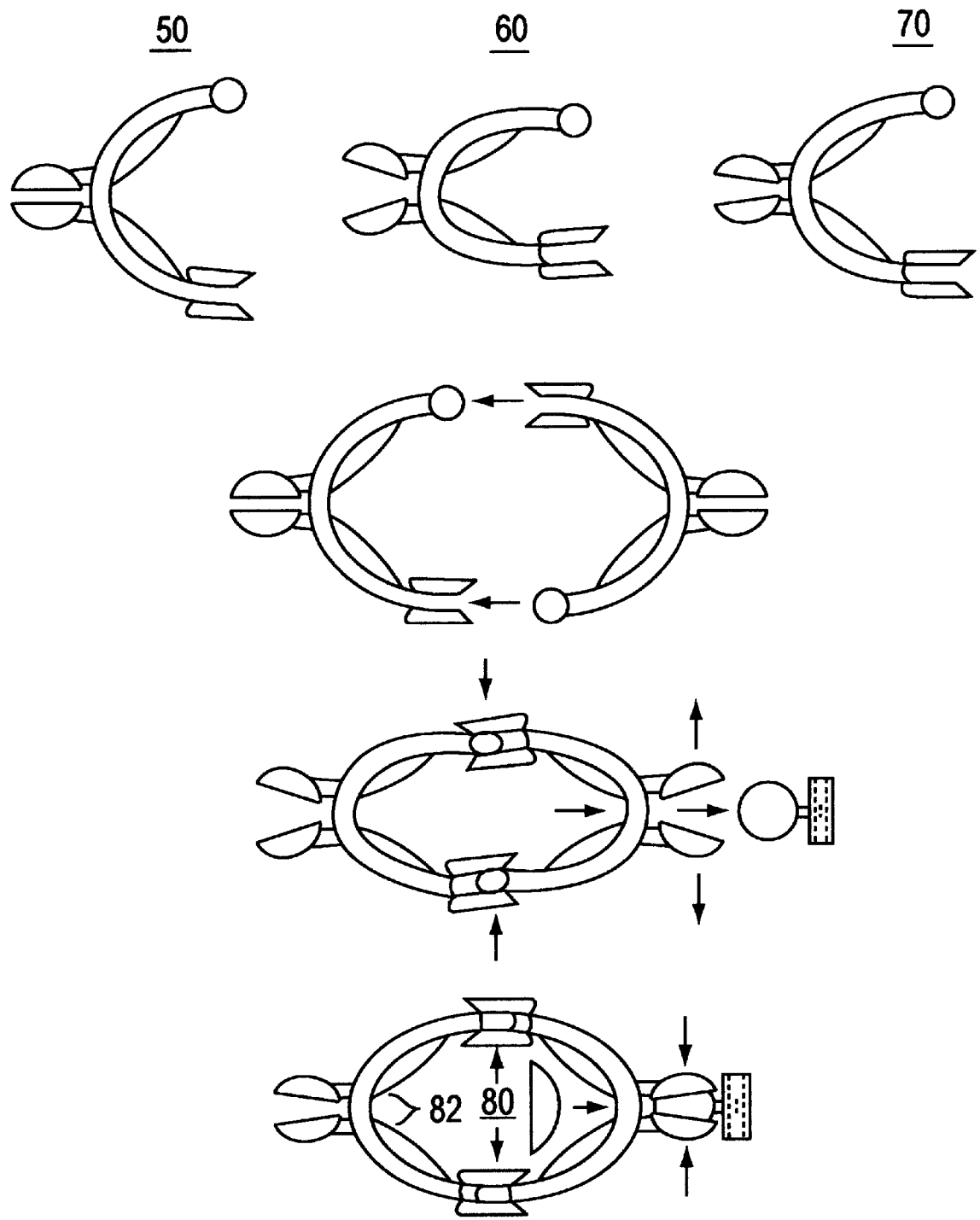
FIG. 8 shows the function of the hinge assemblies and wedge lock of the second preferred embodiment of the invention.

The function of the arcs is shown in FIG. 8. The arcs are cast in a "stretched" position (50) in order to provide tension when working. The cups of any arc can be spread to an open position (60) by squeezing the ends of the arc toward each other to flex the arc at its flex point. Spreading the cups allows the master ball to be placed between them. When the squeezing pressure on the ends of the arc is released, the inner surfaces of the cups engage the surface of the sphere of the master ball and tension caused friction in the working position (70) prevents or retards relative motion between the surface of the sphere of the master ball and the inner surface of the cups. If the tension caused by the form of the arc in the working position fails to prevent rotation of the master ball between the cups, a wedge lock (80) may be used. See FIG. 7 for the structure of the wedge lock and FIG. 8 for it's function. Essentially, the wedge lock engages wedge-lock notches (82) on the concave side of the arcs and, by being pushed into those notches, forces the arc to maintain a flatter position which urges the cups or rings further against the sphere of the master ball.

Figure 9:
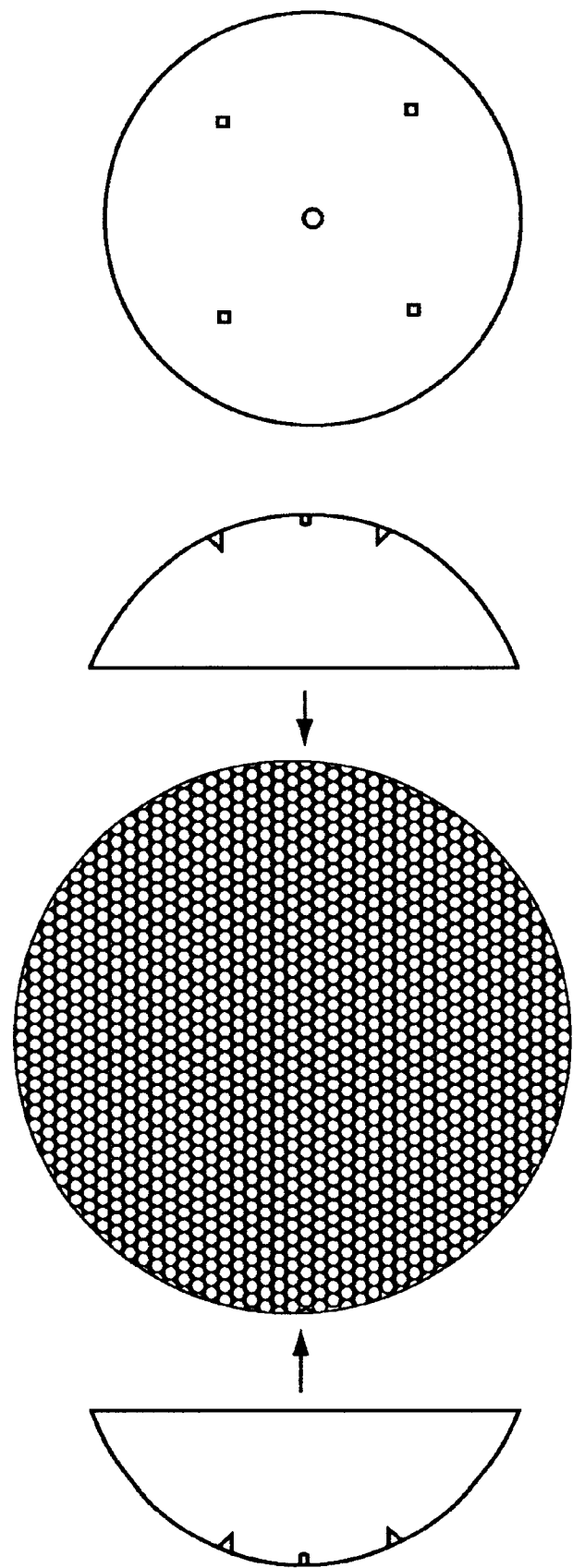
FIG. 9 shows a preferred embodiment in which the cups of the hinge assembly and the sphere of the master ball have mating protuberances and depressions.

In order to better secure the master ball in the cups, one or both of the exterior of the sphere or the interior of the cups may be textured. Alternatively, the surface of the sphere of the master ball and the interior of the cups may have mating protuberances and depressions. See FIG. 9.

Figure 10:
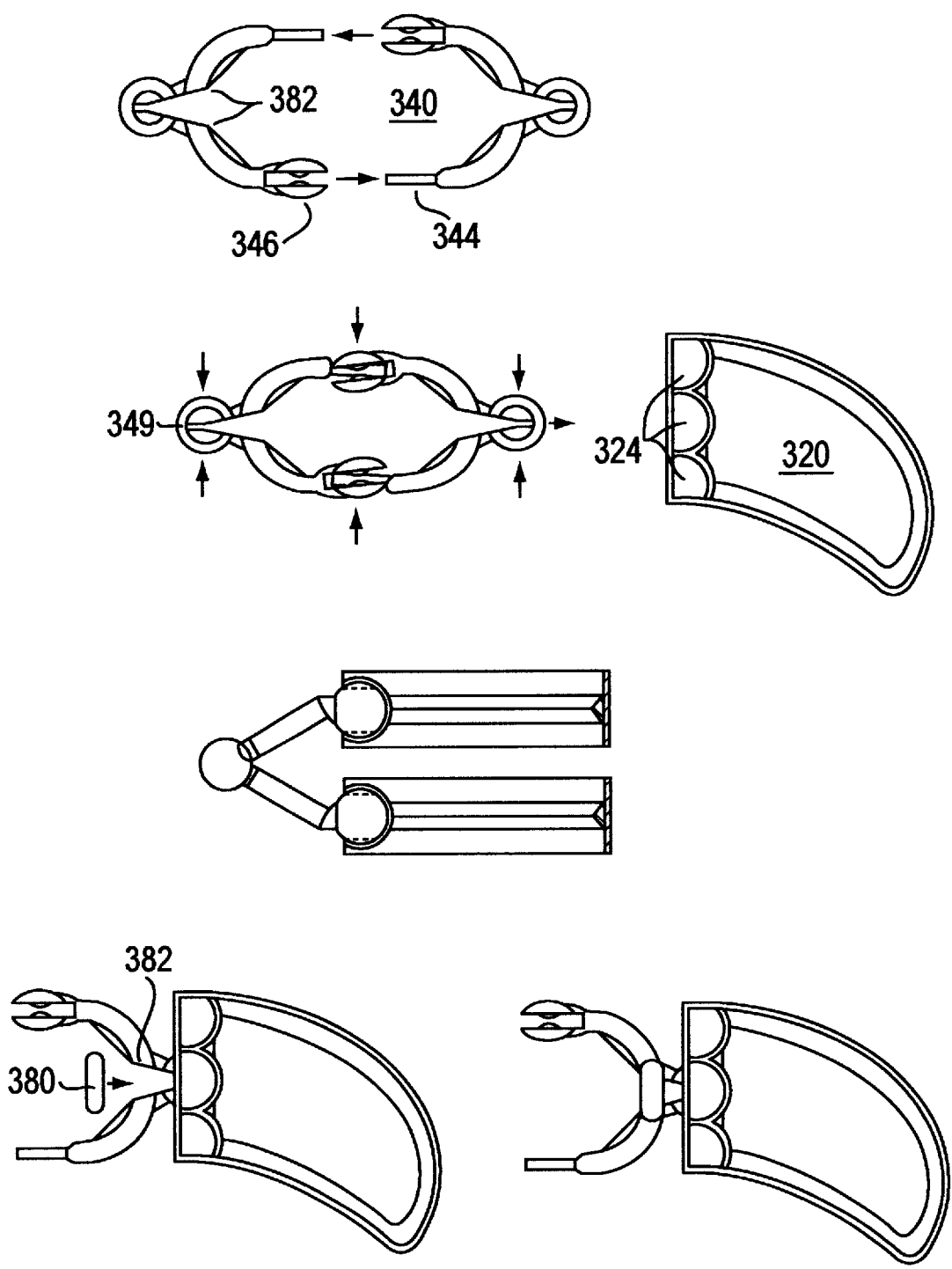
FIG. 10 shows the structure and function of a third preferred embodiment of the dental articulator.

A third preferred embodiment is depicted in FIG. 10. In this embodiment, the attachment sites (324) on the base mold band (320) are substantially spherical sockets and the hinge assemblies (340) have, at the apex of their arcs, a substantially spherical flex point (349). When the arcs are compressed at their ends, the substantially spherical flex point is compressed enough to be placed into the socket of the attachment site (324). Once the compression on the arc is released, the substantially spherical flex point expands to fill the socket of the attachment site with sufficient force for friction to prevent ready relative movement between them. If release of the compression on the arc is insufficient, alone, to inhibit relative motion between the substantially spherical flex point and the socket of the attachment site, then a wedge lock (380) may be forced between wedge lock notches (382) to further expand the substantially spherical flex point and secure it in the socket. In the embodiment of FIG. 10, the hinge assemblies may have a hinge ring (344) which mates with a hinge clip (346) to form each hinge.

Figure 11:
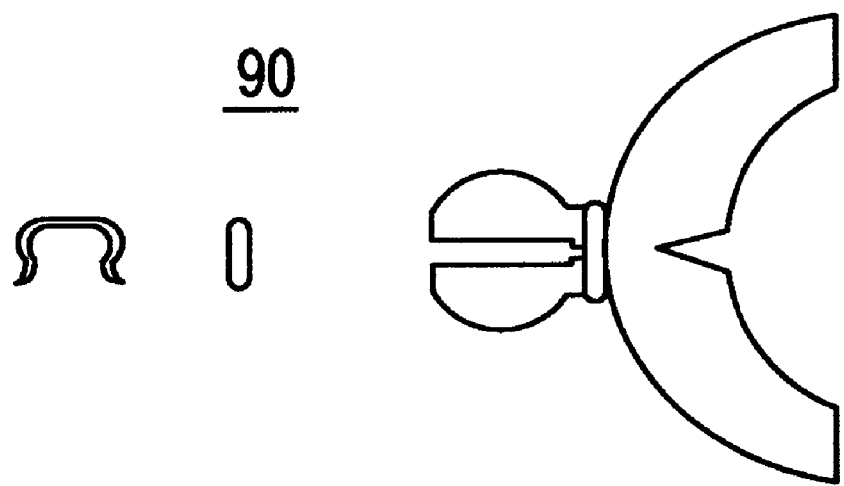
FIG. 11 shows a preferred embodiment in which an elastic clip or a cinch is used to urge the cups or rings of the hinge assembly against the surface of the master ball to prevent relative motion between the hinge assembly and the master ball.
Figure 11:
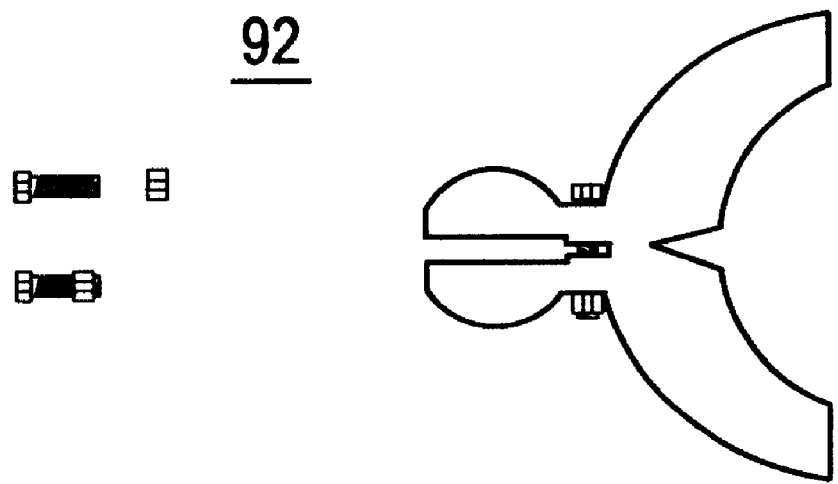

FIG. 11 shows yet another preferred embodiment, in which an elastic clip or band (90) or a cinch (92) is used to urge the cups or rings of the hinge assembly against the master ball. This further prevents relative motion between the cups or rings and the sphere of the master ball. The elastic clip or band is placed over the necks of the cups or rings to urge them together. The cinch may be applied through holes in the cup necks.

It is to be understood that the foregoing embodiments are exemplary and explanatory only and are not restrictive of the invention. Various changes may be made to the embodiments described above by one of skill in the art without departing from the scope of the invention, as defined by the following claims.

I claim:

1. An apparatus for mounting and articulating a dental model comprising upper teeth mounted in an upper base and lower teeth mounted in a lower base, the apparatus comprising:
    a first substantially inflexible band for encircling the upper base, the first substantially inflexible band further comprising
        a first retaining means for extending into and securing the upper base and
        a first attachment site on an outer surface of the first substantially inflexible band,
    a second substantially inflexible band for encircling the lower base, the second substantially inflexible band further comprising
        a second retaining means for extending into and securing the lower base and
        a second attachment site on an outer surface of the second substantially inflexible band,
    a pair of spheres with attached mechanical means for fixedly securing each sphere to one of the first or second attachment sites, and
    a hinge assembly comprising
        a pair of elastic arcuate arms connected at their ends by a hinge mechanism and
        a pair of grips at the apex of each arcuate arm, each grip of the pair facing each other and being shaped to grip the surface of a sphere,
        wherein each arcuate arm can be flexed by squeezing its ends toward each other to spread the pair of grips sufficiently to allow insertion one of the pair of spheres between the pair of grips and, when the squeezing is released, the grips engage the surface of the sphere to fixedly secure the sphere by friction.

2. The apparatus of claim 1, wherein the grips have a ring shape.

3. The apparatus of claim 1, wherein the grips have a cup shape.

4. The apparatus of claim 1, wherein at least one of the spheres and the grips are textured.

5. The apparatus of claim 1, wherein the grips and spheres have mating protuberances and depressions on their contacting surfaces.

6. The apparatus of claim 1, wherein the first and second attachment sites comprise cavities in the outer surface of the first and second substantially inflexible bands, the cavities having their narrowest point proximal to the outer surface and their widest point distal to the outer surface; and the mechanical means for fixedly securing each sphere is at least one barb wider than the narrowest point of the cavities, wherein the barb is constructed of a material that allows the barb to be forced past the narrowest point of the cavities to anchor the barb in the cavities.

7. The apparatus of claim 1, wherein the first and second attachment sites comprise a raised portion of the outer surface of the first and second substantially inflexible bands, the raised portions being narrowest proximal to and widest distal to the outer surface; and the mechanical means for fixedly securing each sphere is a C-shaped clasp that engages the raised portion.

8. The apparatus of claim 7, wherein the raised portion further comprises transverse grooves and the C-shaped clasp has matching tongues for engaging the grooves.

9. The apparatus of claim 1, wherein the hinge assembly further comprises a removable brace which prevents flexing of the arcuate arms by squeezing the ends of the arms together.

10. The apparatus of claim 1, wherein the hinge assembly further comprises a pair of removable clamps, each clamp preventing the spreading of the grips in one pair of grips.

11. The apparatus of claim 1, wherein the hinge assembly further comprises a pair of cinches, each cinch urging the grips in one pair of grips toward each other.

12. An apparatus for mounting and articulating a dental model comprising upper teeth mounted in an upper base and lower teeth mounted in a lower base, the apparatus comprising:
    a first substantially inflexible band for encircling the upper base, the first substantially inflexible band further comprising
        a first retaining means for extending into and securing the upper base and
        at least one substantially spherical socket with an opening in an outer surface of the first substantially inflexible band,
    a second substantially inflexible band for encircling the lower base, the second substantially inflexible band further comprising
        a second retaining means for extending into and securing the lower base and
        at least one substantially spherical socket with an opening in an outer surface of the second substantially inflexible band, and
    a hinge assembly comprising
        a pair of elastic arcuate arms, each arm having an apex which forms a partial sphere sized to fit the substantially spherical socket, and
        a hinge mechanism connecting the arcuate arms at their ends, wherein each arcuate arm can be flexed by squeezing its ends toward each other to compress the partial sphere sufficiently to allow insertion the partial sphere into the socket and, when the squeezing is released, the partial sphere expands to fixedly secure the partial sphere in the socket by friction.

13. The apparatus of claim 12, wherein a surface of at least one of the partial sphere and the substantially spherical socket is textured to increase the friction between them.

14. The apparatus of claim 12, wherein the partial spheres and the substantially spherical socket have mating protuberances and depressions on their contacting surfaces.

15. The apparatus of claim 12, wherein each elastic arcuate arm further comprises a pair of opposing wedge lock anchor sites on the concave side of the arcuate arms and centered on the apex, and the apparatus further comprises a wedge lock, which is sized to apply an expansion pressure on the elastic arcuate arm when placed between the wedge lock anchor sites.

16. A method of forming a dental model comprising tooth shapes in a cured substrate, the method comprising:

providing a substantially inflexible band for enclosing the cured substrate, the band having a retaining means for extending into and securing the cured substrate, providing a flexible cap, placing the substantially inflexible band on the flexible cap to provide a mold having the flexible cap as its bottom, the inflexible band as its sides and the retaining means extending into the void defined by the bottom and sides, placing an uncured substrate in the mold with the retaining means extending into the uncured substrate, anchoring the tooth shapes in the uncured substrate, allowing the substrate to cure, and removing the flexible cap from the cured substrate.

* * * * *